US010261073B2

(12) United States Patent
Bechstein et al.

(10) Patent No.: US 10,261,073 B2
(45) Date of Patent: Apr. 16, 2019

(54) COMPARTMENTALIZED INTEGRATED BIOCHIPS

(71) Applicant: The Board of Trustees of the Leland Stanford Junior University, Palo Alto, CA (US)

(72) Inventors: Daniel Jacob Benjamin Bechstein, Mountain View, CA (US); Shan X. Wang, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/046,605

(22) Filed: Oct. 4, 2013

(65) Prior Publication Data

US 2014/0100141 A1 Apr. 10, 2014

Related U.S. Application Data

(60) Provisional application No. 61/711,869, filed on Oct. 10, 2012.

(51) Int. Cl.
*B01L 3/00* (2006.01)
*G01N 33/53* (2006.01)

(52) U.S. Cl.
CPC ........ *G01N 33/5302* (2013.01); *B01L 3/5027* (2013.01); *B01L 2200/0689* (2013.01); *B01L 2200/12* (2013.01); *B01L 2200/16* (2013.01); *B01L 2300/0636* (2013.01); *B01L 2300/0816* (2013.01); *B01L 2300/0883* (2013.01)

(58) Field of Classification Search
CPC ............... G01N 33/5302; B01L 3/5027; B01L 2200/12; B01L 2200/16; B01L 2300/0636; B01L 2300/0816; B01L 2300/0883
See application file for complete search history.

(56) References Cited

U.S. PATENT DOCUMENTS

| 6,537,506 | B1 * | 3/2003 | Schwalbe et al. | ............ 422/130 |
|---|---|---|---|---|
| 8,182,635 | B2 | 5/2012 | Ayliffe et al. | |
| 8,383,060 | B2 | 2/2013 | Dekker et al. | |
| 2002/0124896 | A1 * | 9/2002 | O'Connor | ............... B01F 5/064 137/833 |
| 2004/0112529 | A1 * | 6/2004 | Karlsson | .............. B01J 19/0093 156/306.6 |

(Continued)

OTHER PUBLICATIONS

Shaikh, Kashan A., et al. "A modular microfluidic architecture for integrated biochemical analysis." Proceedings of the National Academy of Sciences of the United States of America102.28 (2005): 9745-9750.*

(Continued)

*Primary Examiner* — Robert J Eom
(74) *Attorney, Agent, or Firm* — Lumen Patent Firm (57) ABSTRACT

An integrated microfluidic biochip is provided that includes a microfluidic device, where the microfluidic device includes hollow structures, where at least one the hollow structure includes an output at a bottom surface of the microfluidic device, and a sensor plate, where the sensor plate comprises a plurality of independent surface sensors, where the microfluidic device is sealably attachable to the sensor plate, where the hollow structure output abuts the surface sensor when the microfluidic device is attached to the sensor plate.

10 Claims, 5 Drawing Sheets

(56) References Cited

U.S. PATENT DOCUMENTS

2005/0255001 A1* 11/2005 Padmanabhan et al. ....... 422/73
2008/0247907 A1* 10/2008 Bergman .......... B01L 3/502746
                                                        422/68.1
2009/0142745 A1*  6/2009 Breidenthal ........ B01F 11/0045
                                                          435/3
2011/0150705 A1*  6/2011 Doyle et al. ................ 422/82.02
2011/0223612 A1*  9/2011 Wang ................... G01N 27/745
                                                          435/7.1

OTHER PUBLICATIONS

Datta, Proyag, et al. "Development of an integrated polymer microfluidic stack." Journal of Physics: Conference Series. vol. 34. No. 1, IOP Publishing, 2006.*

* cited by examiner

COMPARTMENTALIZED INTEGRATED BIOCHIPS

CROSS-REFERENCE TO RELATED APPLICATIONS

This application claims priority from U.S. Provisional Patent Application 61/711,869 filed Oct. 10, 2012, which is incorporated herein by reference.

STATEMENT OF GOVERNMENT SPONSORED SUPPORT

This invention was made with Government support under grant (or contract) no. CA143907 and CA151459 awarded by the National Institutes of Health (NIH). The Government has certain rights in this invention.

FIELD OF THE INVENTION

The present invention relates generally to interfacing between microfluidics and multiple sensors or sensor arrays. More particularly, the invention relates to compartmentalized biosensors for analytical biochemistry, diagnostics and immunoassays.

BACKGROUND OF THE INVENTION

Sensor arrays for molecular detection are often desired to contain large numbers of individual sensors. In principle every sensor can be used to detect a different target analyte, but chemical and biological cross reactivity and different dynamic ranges reduce the marginal benefit of each additional sensor of the array.

There is a broad range of biosensors, which are analytical devices and can detect biological analytes with a broad range of detection mechanisms. Biosensors are key elements in diagnostic devices or platforms as they convert a biological signal (e.g., concentration of a target analyte) into an externally measurable signal.

Microfluidic devices are able to perform analytical operations, with a high throughput—essentially through parallelization—and low reagent use. Microfluidic chips use all kinds of materials that contain fluids in a micrometer scale, most commonly polymers (e.g. PDMS, PMMA, Polyolefins), glass and silicon. Most microfluidic analytical devices used for biological analyses employ optical detection rather than solid-state based biosensors.

While there is a broad range of biosensor chips and microfluidic devices available for analytic purposes, very few devices combine both biosensors with microfluidics. Such combined systems have the advantage of directly analyzing biological samples, e.g., by performing microfluidic bioassays.

The biosensors with irremovably fabricated microfluidic features/microfluidic devices on the sensor solid support or similarly a sensor embedded in a microfluidic device are typically fabricated in a process having several formation steps resulting in a device that at least structures microfluidic features on the sensor surface and typically encloses the biosensor in the microfluidic system.

Due to the rapid expansion of solid-state fabrication technologies for substantially planar devices, multiple sensors on a single sensor solid support (e.g. sensor arrays) become more economical to manufacture. With this many sensors on a solid support, a single compartment approach, the marginal benefit of each additional sensor becomes smaller as the higher the number of sensors get. Added constraints such as cross reactivity between analytes and requirements for adapted dynamic ranges for different analytes become more complex to handle with each additional analyte. Therefore, the ability to gain useful information from an additional sensor by detecting an additional analyte decreases. This leads to an effective limit on the number of samples and analytes that can be measured with a single device. In other words, not all of the sensors can be put to their best possible use.

Current microfluidic technology covers the sensor solid support in only one compartment and has not kept up with addressing these sensors more individually. Therefore, there is a need in the art to compartmentalize specific sensors, separated from other sensors, on a substantially planar sensor solid support to get the best use out of each sensor in a sensor support.

Using sensors in specific biological target molecule detection requires to specifically functionalize the individual sensors in sensor arrays to detect the specific target molecules. This required individual functionalization of each sensor in sensor arrays is not practical when multiple sensors in a single closed compartment need to be functionalized with different processes/reagents. Therefore there is a need in the art to functionalize specific sensors individually before compartmentalization into more than one compartments.

SUMMARY OF THE INVENTION

To address the needs in the art, an integrated microfluidic biochip that includes a microfluidic device, where the microfluidic device includes hollow structures, where at least one the hollow structure includes a reagent interface at a bottom surface of the microfluidic device, and a sensor plate, where the sensor plate comprises a plurality of independent surface sensors, where the microfluidic device is sealably attachable to the sensor plate, where the hollow structure reagent interface abuts the surface sensor when the microfluidic device is attached to the sensor plate.

According to one aspect of the invention, the microfluidic device has a plurality of layers, where the plurality of layers is interconnected by hollow vias. In one aspect, the interconnected plurality of layers are capable of sealably interfacing a microfluidic chip, where the microfluidic chip comprises dimensions that are larger than dimensions of the sensor plate surface. In a further aspect, i) the hollow structures, ii) the surface sensors, iii) the microfluidic chip, i) and ii), i) and iii), ii) and iii), or i) and ii) and iii) are disposed to compartmentalize separate analytes.

In another aspect of the invention, the microfluidic device includes a surface interface layer, a control layer and a fluid logic layer, where the surface interface layer is removably attached to the sensor plate, where the control layer comprises control channels, where the control channel comprises i) a valve, ii) a pump capable or i) and ii), where the control channel is capable of controlling fluid in the fluid logic layer by closing and opening the channels in the fluid logic layer.

According to a further aspect of the invention, each independent surface sensor includes an independent capture molecule for detecting separate analytes.

In one aspect of the invention, the surface sensors include a range of sizes.

In yet another aspect of the invention, the hollow structures are capable of isolating individual surface sensors or groups of surface sensors from other surface sensors on the sensor plate.

According to one aspect of the invention, the surface sensors are disposed in an array of surface sensors.

In a further aspect of the invention, the microfluidic device includes microfluidic valves, where the microfluidic valves are capable of dynamically programming the hollow structures.

DETAILED DESCRIPTION

A device and method of forming compartmentalization of a plate sensor solid support through a microfluidic device with hollow structures at its bottom surface is provided. The microfluidic device can be fabricated separately and attached to the plate sensor solid support after surface functionalization. This allows the use of sensor arrays with compartments of varying sizes that match their intended use.

Some aspects of various embodiments of the current invention include a substantially planar plate sensor solid support with multiple individual surface sensors or sensor groups. The plate sensor solid support can be fabricated using IC/VLSI, MEMS, magnetic or glass processes, for example, that can be prepared to detect specific target molecules, where the preparation includes pre-functionalization of one or more sensors. In one embodiment, the microfluidic chip has hollow structural elements at its bottom surface to align with individual sensors of the plate sensor array or align with sensitive areas or segments of the sensor. In another embodiment, the invention includes partitioning the sensors into groups on the plate sensor solid support into distinct areas. According to another embodiment, a seal between sensor solid support and microfluidic chip is provided.

According to further embodiments, the plate sensor array can be individually fabricated from the microfluidic chip according to preferred manufacturing processes, where the plate sensor surface can be functionalized (e.g. by a robotic spotter) before the microfluidic chip is combined with the sensor.

According to another embodiment of the invention, the partitioning of sensors into individual groups enables separated sensing chambers in which different processes are performed. This allows multiplexed use of the plate sensor, so that one sensor array can be used for multiple experiments and/or with different reagents and/or samples. One key advantage is the ability to separate detection of two species, for example, which detection processes show cross reactivity through compartment walls into separate groups, thus eliminating the detection cross reactivity. Another key enablement is individual adjustment of the dynamic range of each sensor group. The reactions can be grouped to similar dynamic ranges and each group's sensors' dynamic range can be individually controlled, for example by dilution of the reaction species.

In addition to microfluidic components, logic and/or actuation on chip, sample preparation and dilution stages, and samples and reagents routing to the sensor interface can be included in the microfluidic chip, resulting in an integrated biochip.

Turning now to the plate sensor, the individual sensors are surface sensors, which can detect target molecules. Integrated sensors can be fabricated using IC/VLSI, MEMS, magnetic fabrication and/or similar processes, which relate to a multitude of sensing mechanisms: electrical, mechanical, magnetic or a combination of them.

According to a further embodiment, the sensor surface can be functionalized with capture molecules to capture and detect specifically certain bound analyte, such as molecules and particles for example. In one exemplary embodiment, other reagents might need to be supplied to gather a useful non-biological signal such as fluorescence, magnetic tags, etc. This non-biological signal can then be sensed by a specific sensing/transduction mechanism and typically leads to an electrical signal output.

In one exemplary embodiment, an 8×8 Array of 64 GMR spin-valve sensors is used, which are individually pre-functionalized with different capture molecules (e.g., for biological molecule detection these capture molecules can be antibodies, antigens, or oligonucleotides: antibodies to capture antigens, antigens to capture antibodies and oligonucleotides to capture complementary strands) using a robotic spotter.

In another embodiment, the sensor surface can be functionalized with analytes with a robotic spotter. The analytes are quantified by additional reagents in a format called reverse phase array.

Figure 1A:
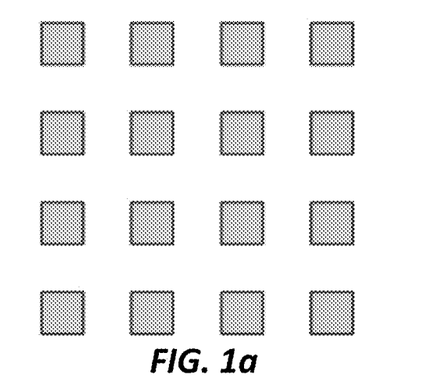
FIGS. 1a-1c show a) Magnetic sensor array schematic, b) regular shaped compartmentalization structures in the same orientation containing equal numbers of sensors, c) differently shaped compartments for various numbers of sensors, according to embodiments of the invention.
Figure 1B:
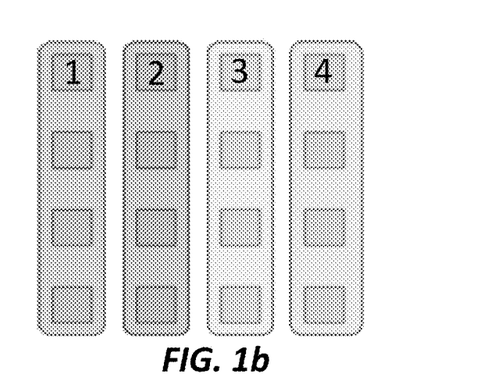
Figure 1C:
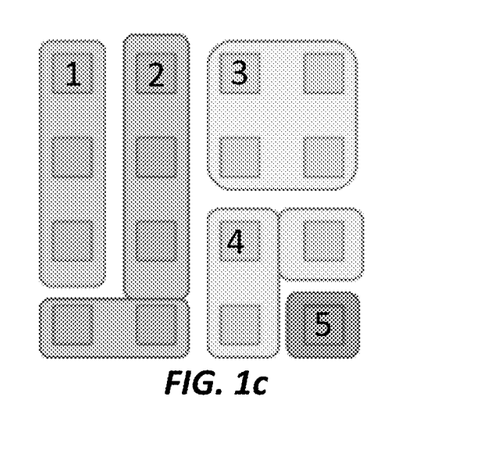

Turning now to compartmentalization of the planar sensor into sensor groups, the individual sensors are partitioned on the planar sensor surface into several compartments or groups, with each group having one or multiple sensors being physically separated from the other groups. The groups can have different sizes, shapes and/or numbers of sensors (FIGS. 1a-1c).

Figure 2A:
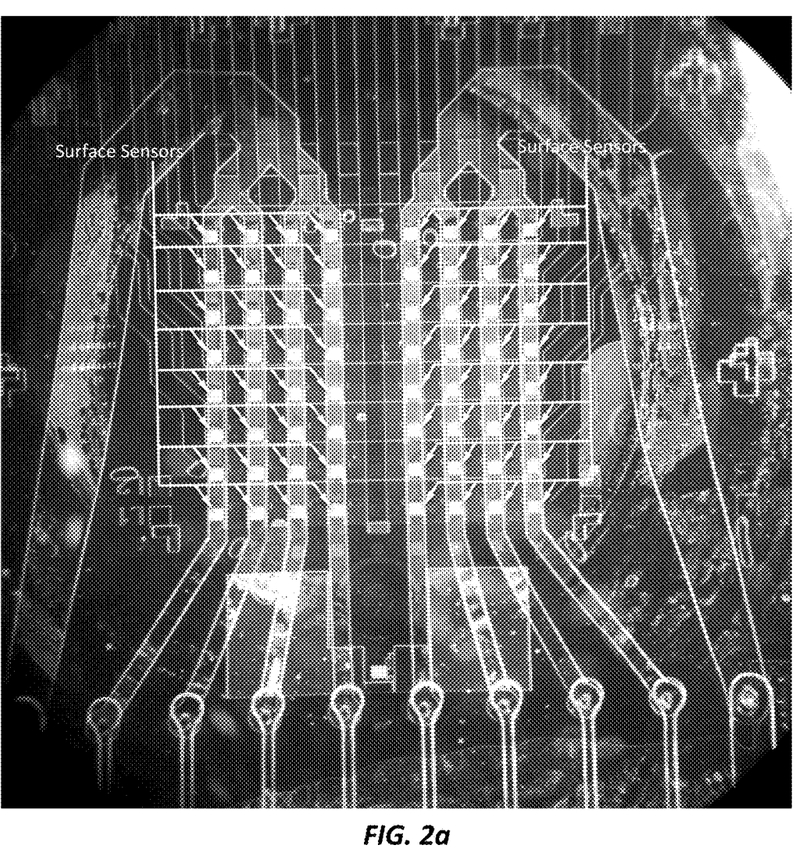
FIGS. 2a-2c show sensor arrays compartmentalized into channels with individual sensors per channel, fluid containing sample and/or reagents are introduced into each of the channels covering the individual sensors, according to embodiments of the invention.
Figure 2B:
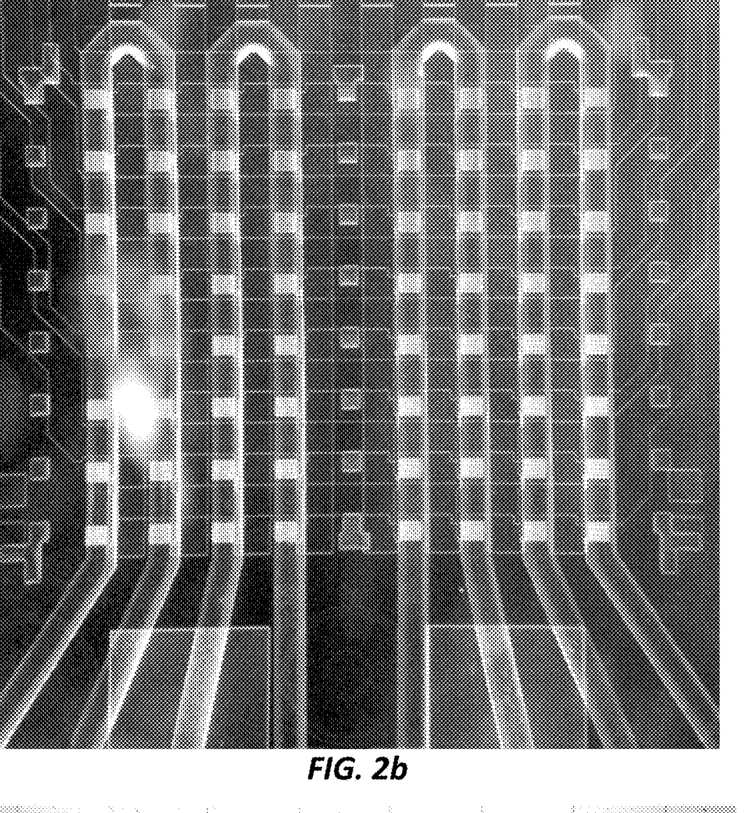
Figure 2C:
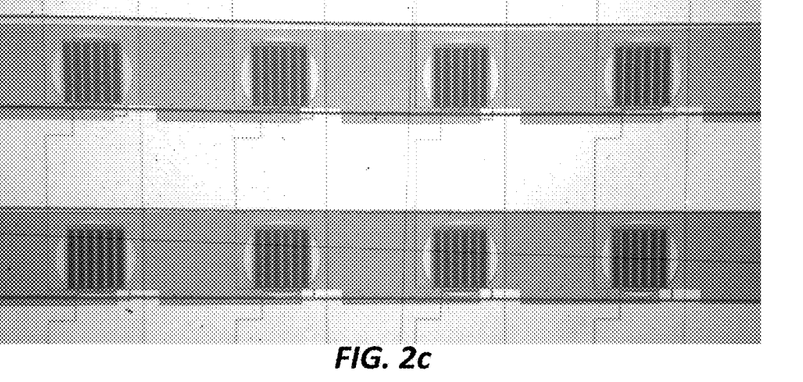

In one embodiment, the compartmentalization of sensors is carried out by hollow features (e.g., channels, wells) above the individual sensors, defining the sensor groups, walls between these hollow features separate individual groups of sensors, where FIGS. 2a-2c show sensor arrays compartmentalized into channels with individual sensors per channel. Here, a fluid containing sample and/or reagents are introduced into each of the channels covering the individual sensors, according to embodiments of the invention. The compartments are created either as part of the microfluidic chip by structuring a microfluidic layer to have specific structured cavities, or an individual component (e.g. structured soft PDMS sheet) that can be aligned between the sensor and the microfluidic chip to have the specific structured cavities or part of the sensor itself (e.g., by patterning a layer of material (Photoresist: SU-8, SiO2, etc) on the planar sensor in a shape that forms the groups by specific structured cavities, or a combination of two or three of the above. These cavities form the compartments above the individual sensors and are connected to the remainder of the microfluidic chip.

One embodiment uses the partitioning as part of the microfluidic chip. Each group of sensors is brought in contact with the same environment, that is reagents in contact with sensors or processing steps, and separated from the other groups. Each sensor in the group can be used for a different purpose, for example analyte detection, positive control, negative control, or as a redundant sensor. Multiple different analytes can be detected per group, at least one dedicated sensor per analyte is necessary for this. The partitioning enables multiplexed use of the sensor array, as one group of sensor can be individually used for one experiment, that is sensing environment, sample, dilution of sample, or set of reagents, without affecting the other sensors. This approach allows multiple samples such as different body fluids, dissolved tissue samples, dissolved excrement sample, etc. to be analyzed for multiple analytes without cross reactivity, where the invention enables spacing out potentially cross reactive detection schemes into separate compartments, and with adjustable dynamic ranges by individual dilution to match sensor dynamic range.

The individual compartments have at least one inlet and outlet and can be microfluidically directly routed to layers in the microfluidic chip by one or more microfluidic layer interconnections, or routed on the sensor solid support, or at a different location routed to layers in the microfluidic chip. The outlets downstream of the sensor for waste can be merged, to save space on a chip.

Figure 2D:
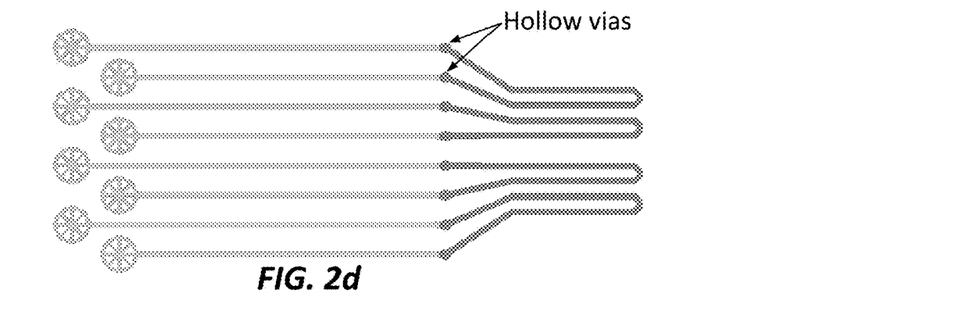
FIG. 2d shows a schematic drawing of a microfluidic chip having eight inlets (far left, cartwheel shaped circles), each routed over 8 parallel sensor rows and two outlets each combining the used reagents merged after flowing through the sensor channels, and dashed lines denoting different layers that enable routing channels in a microfluidic chip over the sensor solid support, according to embodiments of the invention.
Figure 2E:
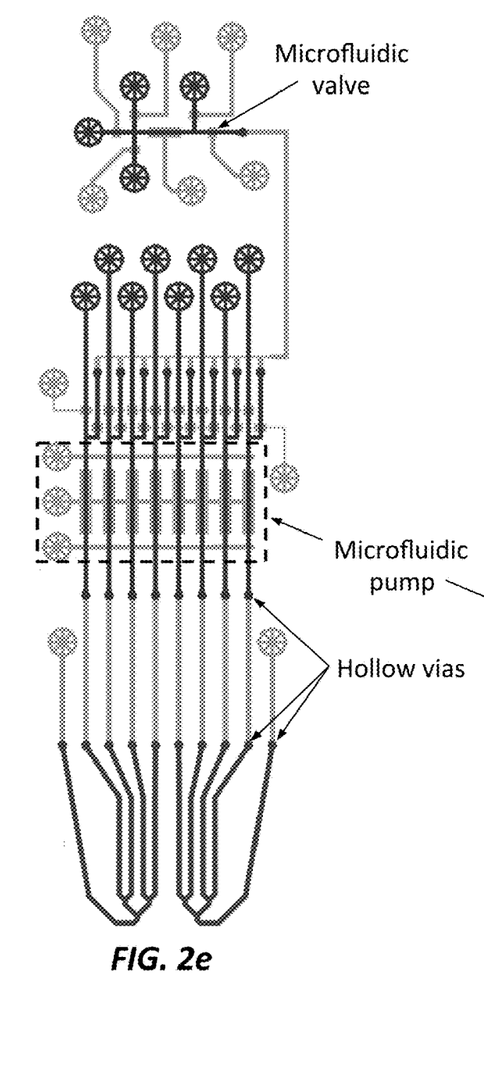
FIG. 2e shows a dilution generator with inlet logic to switch individual inlets using a limited number of connectors, according to embodiments of the invention.
Figure 2F:
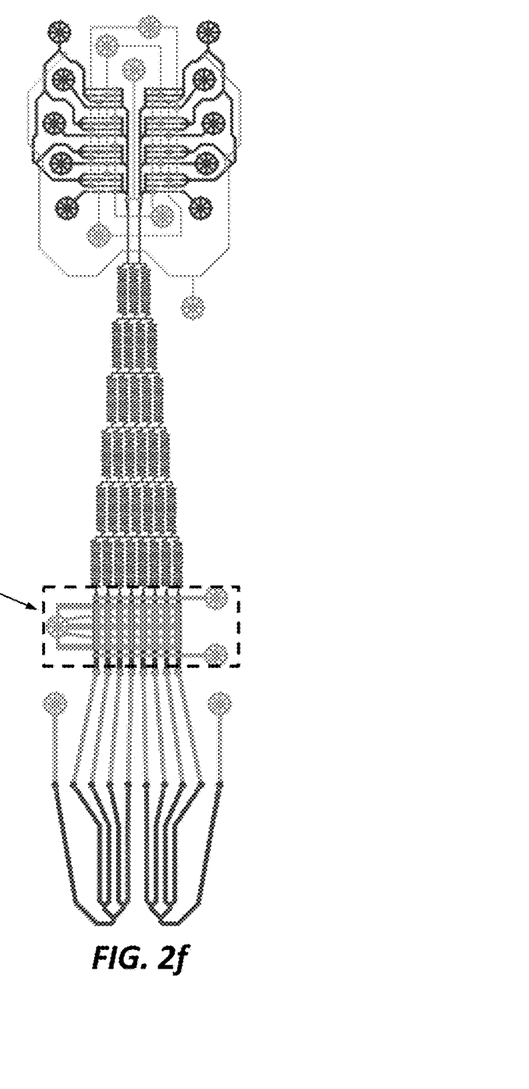
FIG. 2f shows integration of the microfluidic chip and the sensor into a cartridge. The clamping pad provides pressure to the microfluidic chip through fixing the distance of the biosensor and the clamping pad, thus compressing the microfluidic chip, whose elasticity leads to the pressure seal, according to embodiments of the invention.

FIG. 2d shows a schematic drawing of a microfluidic chip having eight inlets (far left, cartwheel shaped circles), each routed over 8 parallel sensor rows and two outlets each combining the used reagents merged after flowing through the sensor channels, and dashed lines denoting different layers that enable routing channels in a microfluidic chip over the sensor solid support, according to embodiments of the invention. FIG. 2e shows a dilution generator with inlet logic to switch individual inlets using a limited number of connectors, according to embodiments of the invention. FIG. 2f shows integration of the microfluidic and the sensor into a cartridge. The clamping pad provides pressure to the microfluidic chip through fixing the distance of the biosensor and the clamping pad, thus compressing the microfluidic chip, whose elasticity leads to the pressure seal, according to embodiments of the invention.

In another embodiment microfluidic compartments and/or connections leading to the sensor/compartments can be dynamically programmed, for example by microfluidic valves to form openings, combining individual compartments, or closures for dividing a compartment. This enables a flexible approach of a programmable interface to the sensor.

Regarding the microfluidic chip, the chip includes two or more of the following elements: sensor/partitioning interface, routing, processing & logic, inlets. The microfluidic chip can be fabricated in soft lithography, for example PDMS and similar processes, or can be fabricated in other processes such as injection molding and laser cutting and using other materials. Harder non-deformable materials (such as PMMA, glass, polyolefin, etc.) can also be used instead of soft materials or in combination with soft materials.

For the sensor/partitioning interface, the microfluidic chip has an interface to the partitioning of the sensors, which is either embedded in the microfluidic chip or separate. In case it is embedded in the microfluidic chip, its hollow structures are in the bottom layer of the microfluidic chip and form a hollow space when placed on a planar solid support (e.g. the sensor). These hollow spaces are connected to the routing at one or multiple other layers within the microfluidic chips through connections between layers (vias). In case the partitioning of the sensors is not embedded in the microfluidic chip, the microfluidic chip has a planar, unpatterned bottom layer, but still has via connections in this layer to the routing at one or multiple other layers within the microfluidic chip.

The purpose of the interface is to deliver reagents (e.g. sample, analytes, etc.) to well/channel covering one or multiple sensors.

Figure 3:
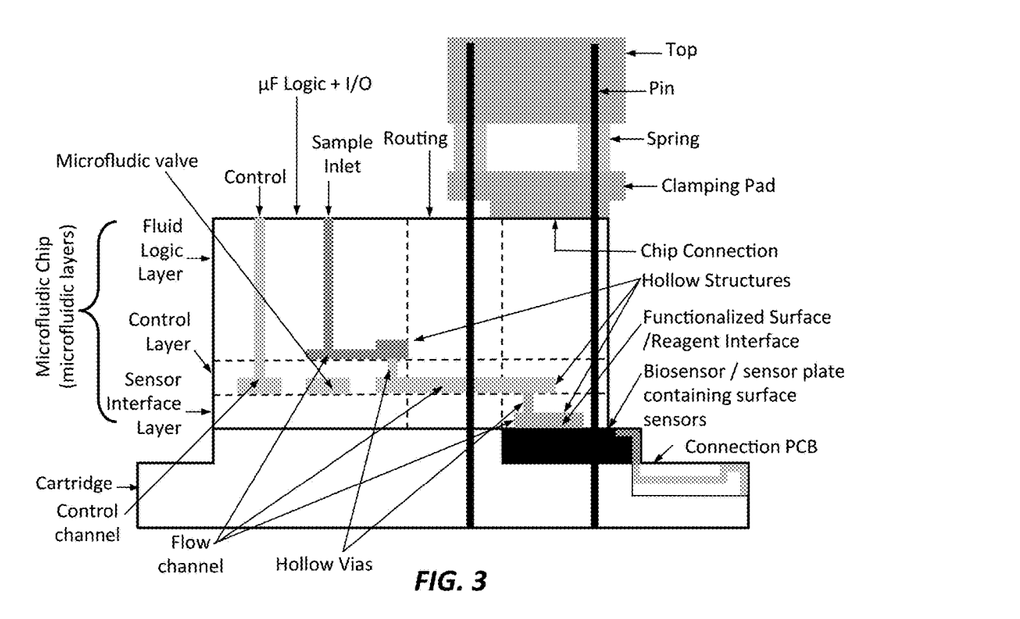
FIG. 3 shows microfluidic chip with embedded routing connected to the sensor, the microfluidic channels denote control lines and sample/reagent flow through chip to the sensor on a PCB holder, according to embodiments of the invention.

FIG. 3 shows microfluidic chip with embedded routing connected to the sensor, the microfluidic channels denote control lines and sample/reagent flow through chip to the sensor on a PCB holder, according to embodiments of the invention.

In the microfluidic chip of the current invention, components of microfluidic chips are connected in plane by microfluidic channels. However, due to the multilayer microfluidic chip embodiment, as shown in FIG. 3, with an interface to the partitioned sensor, fluid needs to be routed through the bottom layer. Therefore interlayer fluidic routing becomes necessary.

The routing from the interface layer to a middle layer allows the extension of the microfluidic chip over the size of the sensor solid support (see FIG. 3). Where the microfluidic chip is extended over the surface of the sensor solid support, a support carrier may be applied to hold the microfluidic chip straight, support it from the bottom and prevent bending. Additionally the support carrier and the biosensor might be placed on a secondary carrier structure (such as a PCB) as a common base to prevent differential movement between the biosensor and the support carrier and as such also of the microfluidic chip.

In a further embodiment, different microfluidic layers can have different heights or channel shapes, with some layers being easier or harder to collapse. The easier to collapse ones are useful for valve designs, whereas the harder to collapse ones resist closing under pressure and are useful for applications where pressure is applied. This allows on to choose the most desirable layer for the fluid path to take, and to design valves and pressure resistant segments in one line.

In one embodiment for the analysis of separate samples on one single sensor solid support, parallel processing and preparation pathways from the inlet to the interface are required to separate the different samples and avoid cross-contamination.

Turning now to processing and logic, one key advantage of microfluidics is the integration of sample preparation. Varying microfluidic passive components (such as mixer, splitting and merging of channels, dilution generators, filters, etc.) and active components (e.g., valves) are integrated on the microfluidic chip to create a sample preparation/processing stage. The embodiment of FIG. 2e shows the integration of multiple components.

In another embodiment shown in FIG. 2f, one sample is used and analyzed in different compartments at different dilution levels for optimized dynamic range. For this an automatic dilution is created (a dilution series is automatically performed—sample is mixed with dilution buffer) in a dilution generator, embedded in the microfluidic chip.

The compartments are arranged so that the output concentrations match the dynamic ranges, where the smallest dilution is for the highest required concentration in varying dynamic range processes.

Such an approach is also useful for creating a reference signal, or standard curves, i.e., the sensor response for a known analyte at different concentrations/dilutions to compare to sensor data of unknown samples.

A dilution series-generating chip can also be combined with a separate pathway for a different sample. This then allows for creating a dilution series from a known concentration of the target analyte and comparing it directly on one sensor solid support.

After the sample processing all or part of the outputs of the sample generation stage are connected to the different sensor compartments. There can be switchable channels so that specific samples can be taken, while others ignored, which is useful to performing experiments sequentially. Also, this is especially useful if a dilution generator generates a specific dilution gradient with some intermediate generated dilutions and/or side dilution channels not required for the experiment.

Regarding alignment, assembly and seal forming, an important part is the seal between the microfluidic chip and the sensor and/or the partitioning element. The alignment of the individual parts (microfluidic chip, sensor, and eventually the partitioning), typically happens optically guided (e.g., under a microscope). After alignment, the parts need to stay in permanent contact and form a seal.

This seal can be formed in multiple ways. One way is a physical or chemical bond between the individual layers, eventually assisted by a surface treatment (e.g., plasma, chemical) of one or more of the effected surfaces. However this can be challenging due to the functionalization of the sensor, which does not always allow for a good adhesion and typically prohibits additional surface treatment. In this case another option is to form a pressure seal. Through controlled pressure on the microfluidic chip above the sensor solid support, the microfluidic chip is compressed against the sensor solid support or partitioning and forms a pressure seal, that is leakage-free also in experimental setups. Applying the pressure only above the sensor solid support part and not over the whole microfluidic chip ensures that only on parts of the microfluidic chip above the sensor surface and adjacent parts are compressed. This compression will deform the affected microfluidic channels also slightly, however, these channels have a large enough height to not be completely compressed and stay open. It is important for other channels (e.g., pump, valves, etc), which do not have the same compression resistance, to be spaced away from the compression region to be not partially or completely collapsed, impeding their functions.

In one embodiment pressure can be used to provide that seal. A pressure/clamping force between microfluidic chip and sensor can be supplied by either a weight on the microfluidic chip location or by compression of a spring or a spring like element (e.g., a beam, an elastic structure such as the microfluidic chip) but could also be supplied by other pressure or compression sources such as hydraulic or pneumatic pressure.

Regarding the cartridge, it is advantageous to keep the microfluidic chip and the sensor solid support and/or partitioning aligned and sealed in one unit that is easy to use and manipulate. An element that combines this can be a cartridge, which includes at least the microfluidc chip, sensor solid support and the compartmentalization, but could also include more elements such as electrical routing (e.g., PCB), components and connectors, fluidic elements, support structure(s) and compression structure(s). Such a cartridge could also be used to actuate microfluidic valves that can be controlled/actuated by electrical signals (e.g., electrochemical, thermal, magnetical valves).

A compression seal in the cartridge can be implemented by mechanical compression of two substantially planar structures against each other with the microfluidic chip and the sensor solid support/partitioning in between, creating internally a compression that applies a force between the sensor and the microfluidic chip. The embodiment shown in FIG. 3 shows a schematic drawing of a cartridge.

External filters can be added to the cartridge to filter a sample, e.g., blood, other body fluids, and dissolved tissue samples, before or after entering the microfluidic chip.

The cartridge itself can be seen as a fully integrated biochip which could include all or some of the following: actuation, sample processing, routing, electrical interfaces, fluid control interfaces, sample/reagents interfaces, wells, filters, reagents on chip, waste outlet/waste on chip storage, sensing, etc.

For the sensor preparation, the sensor solid support with the individual sensors is functionalized with capture molecules (e.g., antibody or oligonucleotide, for chemical sensing specific chemical group) to specifically capture a target molecule and bind to it. The sensor surface can be blocked afterwards using blocking agents (e.g., 1% BSA in PBS) to reduce non-specific binding of other non-target molecules to the sensor solid support. This blocking step could be also performed post-assembly by flowing blocking agent through the microfluidic chip over the sensor surface.

The functionalized sensor surface is assembled with the microfluidic chip and, if desired, placed in a cartridge. A seal between the sensor and the microfluidic chip and/or partitioning is formed so that the individual compartments are connected to specific microfluidic channels but separated from each other.

Regarding the use in an immunoassay, the sample/samples and reagents are introduced in the microfluidic chip.

The sample is introduced in the preparation stage and desired operations (e.g., dilutions and sample division) are performed as needed before the sample or samples containing the target molecules, e.g., proteins, complementary oligonucleotide strands, and complementary chemical groups are pumped into or through the compartments covering the individual sensors. There, target molecules bind to their specific capture molecules.

Specific detection molecules (e.g., detection antibody, oligonucleotide strands, and specific chemical group) are pumped into or through the compartments covering the individual sensors and bind to the specific target analyte molecules. These detection molecules can have already a specific tag of interest, such as magnetic nanoparticle, attached that can be detected by the sensing method, for example magnetic sensing.

If the detection molecules do not have a tag attached yet, they have a specific chemical group that can form a physical or chemical bond to a tag. In this case, these tags are then subsequently pumped into or through the compartments and binds to the specific chemical group. The presence and quantity of the tags can then be measured by the sensor.

This process can be performed either without any washing steps in between or adding between some or all reagents washing steps. A washing step uses washing buffer (e.g., a PBS based solution) pumped into or through the compartments covering the individual sensors and is used to separate the reagents from each other and to clean the compartment or surfaces from non-specific bound molecules.

The experiment can be performed either in continuous flow, for example having a continuous supply of sample or reagent for the duration of pumping, or the reagents can be pumped into the compartment and the flow then stopped. Then an incubation step follows for a certain time to allow the reagents to bind to the sensor surface. The continuous flow is the preferred embodiment.

Figure 4:
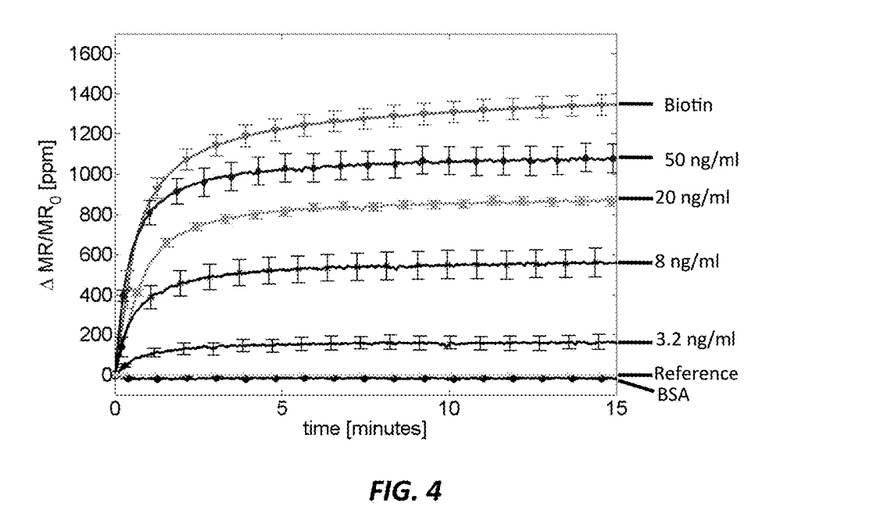
FIG. 4 shows a graph measurable tags in an immunoassay using magnetic sensors and a real time binding signal of the magnetic sensors, according to one embodiment of the invention.

Using magnetic sensors, a real time binding signal of the magnetic tags in an immunoassay is measurable as shown in FIG. 4.

Other aspects of the invention include a device, a planar sensor solid support with multiple individual surface sensors or sensor arrays further referred to as sensor, which could be fabricated using IC/VLSI/MEMS/magnetic/glass/etc. processes, that can be prepared through pre functionalization to detect specific target molecules, a microfluidic chip with hollow structural elements at its bottom surface to align with individual sensors of the sensor array, sensitive areas or segments of the sensor solid support, a compartmentalization of sensors into groups or sensor solid support into distinct areas, and a seal between the sensor solid support and microfluidic chip Some exemplary embodiments are disclosed herein. In one aspect of the invention, the sample or reagents are flowed over the sensor solid support. In another aspect of the invention, the layout of the compartments can be adjustable, through opening or closing valves on chip. According to another aspect of the invention, the sensor measures a concentration or another quantity of the supplied fluid. In a further aspect of the invention, the sensor is used for an immunoassay, oligonucleotide assay or a combination thereof. In one aspect of the invention, the sensor is a magnetic sensor (e.g., GMR and Magnetic Tunnel Junction, Hall-effect sensor). In yet another aspect of the invention, multiple microfluidic components are integrated in the microfluidic chip to be at least partly in contact with the sample and/or reagent fluid. According to one aspect of the invention, microfluidic sample processing steps are integrated (e.g., automatic dilution, mixing of reagents). In another aspect of the invention, the device is incorporated in a cartridge, which includes at least the microfluidc chip, sensor solid support and the compartmentalization. In further aspects of the invention, experiments can be performed sequentially and/or in parallel. According to one aspect of the invention, the sensor can be functionalized before addition of the microfluidic system.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example a wide range of other biological assays (e.g. cell assay, secretion assay, viral titer assay, etc.) can be performed using this approach. In a further example, the sensor is used for chemical sensing, environmental monitoring, or measuring particulates. The sensor could also be a non-magnetic sensor (e.g. field effect transistor-based sensor, optical sensor etc.). The microfluidic chip could have a different structure, multiple layers could include control features controlling flow channels on adjacent layers. Parts of the functionality could be included into the microfluidic chip or taken out and outsourced to additional equipment (e.g. for actuation).

All such variations are considered to be within the scope and spirit of the present invention as defined by the following claims and their legal equivalents.

What is claimed:
1. An integrated microfluidic biochip, comprising:
  a. a microfluidic chip, wherein said microfluidic chip comprises a hollow structure system integrated to a fluid logic layer that is pressure sealed to a control layer, wherein said control layer comprises a valve, wherein said fluid logic layer comprises a fluid logic layer hollow structure system comprising microfluidic logic input/output hollow structures, fluid logic control fluid input hollow structures, a fluid logic routing structure, and fluid logic flow channel hollow structures, wherein said control layer comprises control layer control fluid hollow structures, control layer flow channel hollow structures, control layer control channel hollow vias, and control layer control channels, wherein each said hollow structure system is separated and compartmentalized from another said hollow structure system, wherein each said hollow structure system terminates to a bottom surface of said control layer, wherein each said hollow structure system consists of a single inlet, wherein said control layer is pressure sealed to a sensor interface layer comprising sensor interface hollow vias, sensor layer flow channels, functionalized surface/reagent interfaces; and
  b. a sensor plate, wherein said sensor plate comprises a plurality of sensor arrays, wherein each said sensor array is independently addressable fluidically and electronically, wherein said plurality of sensor arrays are independently coupled to switchable channels, wherein said array of sensors comprise magnetic sensors selected from the group consisting of GMR sensors, magnetic tunnel junction sensors, and hall-effect sensors, wherein each said single inlet is configured to deliver fluid to one said array of sensors, wherein said sensor interface layer is pressure sealed to said sensors according to pressure from a clamping pad, wherein each said compartmentalized hollow structure system abuts one said sensor when said fluid logic layer is attached to said sensor plate, wherein each said independent sensor of said array of sensors comprises an independent and distinct capture molecule deposited thereon.

2. The integrated microfluidic biochip of claim 1, wherein said microfluidic biochip comprises a plurality of microfluidic layers, where said plurality of microfluidic layers are interconnected by hollow vias.

3. The integrated microfluidic biochip of claim 2, wherein said interconnected plurality of layers sealably interface a microfluidic chip, wherein said microfluidic chip is larger than a surface of said sensor plate.

4. The integrated microfluidic biochip of claim 3, wherein i) said array of hollow structure systems, ii) said independent surface sensors, iii) said microfluidic chip, i) and ii), i) and iii), ii) and iii), or i) and ii) and iii) are disposed to hold an analyte, wherein said analyte is held in an individual said hollow structure.

5. The integrated microfluidic biochip of claim 2, wherein said microfluidic layers comprises control channels and flow channels, wherein said control channels comprise i) said valve, ii) said pump or i) and ii), wherein said control channels control fluid in said flow channels in an adjacent said microfluidic layer by operating said pump and by closing and opening said valves in said flow channels in said adjacent microfluidic layer.

6. The integrated microfluidic biochip of claim 1, wherein said array of hollow structure systems are arranged to isolate individual said independent surface sensors or groups of said independent surface sensors from other said independent surface sensors on said sensor plate.

7. The integrated microfluidic biochip of claim 1, wherein said control layer comprises independent microfluidic valves, wherein said independent microfluidic valves are either disposed in an open position or closed position to dynamically program said array of hollow structure systems.

8. The integrated microfluidic biochip of claim 1, wherein said independent and distinct capture molecule comprises an antibody, an antigen, or an oligonucleotide.

9. The integrated microfluidic biochip of claim 1, wherein magnetic sensors are individually addressed electronically by rows of conductive wires and by columns of conductive wires.

10. The integrated microfluidic biochip of claim 1, wherein said magnetic sensors are individually addressed electronically by multiplexing and demultiplexing selector circuits.

* * * * *